(12) United States Patent
Einav et al.

(10) Patent No.: US 10,959,917 B2
(45) Date of Patent: Mar. 30, 2021

(54) MEDICATION CONTAINERS IN MEDICATION DISPENSING SYSTEM

(71) Applicant: Tech Pharmacy Services, LLC, Fort Lee, NJ (US)

(72) Inventors: Omer Einav, Kfar-Monash (IL); Doron Shabanov, Tzur-Yigal (IL); Tamir Ben David, Tel-Aviv (IL); Eyal Livschitz, Givat Shmuel (IL); Thomas A. McKinney, Boonton, NJ (US)

(73) Assignee: Tech Pharmacy Services, LLC, Fort Lee, NJ (US)

( * ) Notice: Subject to any disclaimer, the term of this patent is extended or adjusted under 35 U.S.C. 154(b) by 0 days.

(21) Appl. No.: 16/559,716

(22) Filed: Sep. 4, 2019

(65) Prior Publication Data
US 2020/0323737 A1  Oct. 15, 2020

Related U.S. Application Data

(63) Continuation-in-part of application No. 16/379,835, filed on Apr. 10, 2019, and a continuation-in-part of
(Continued)

(51) Int. Cl.
*G16H 20/13* (2018.01)
*A61J 7/00* (2006.01)

(52) U.S. Cl.
CPC ............ *A61J 7/0076* (2013.01); *G16H 20/13* (2018.01); *A61J 2205/60* (2013.01)

(58) Field of Classification Search
None
See application file for complete search history.

(56) References Cited

U.S. PATENT DOCUMENTS

| 5,405,048 A | 4/1995 | Rogers et al. |
| RE35,743 E | 3/1998 | Pearson |

(Continued)

FOREIGN PATENT DOCUMENTS

| WO | WO 2004/036481 | 4/2004 |
| WO | WO 2005/043440 | 5/2005 |

(Continued)

OTHER PUBLICATIONS

International Search Report and the Written Opinion dated Mar. 22, 2020 From the International Searching Authority Re. Application No. PCT/IB2019/060572. (14 Pages).

(Continued)

*Primary Examiner* — Gene O Crawford
*Assistant Examiner* — Ayodeji T Ojofeitimi

(57) ABSTRACT

A medication dispensing system, comprising one or more medication panels, each having a plurality of docking ports located at a vertical displacement one from another. The medication dispensing system comprises: a plurality of medication container assemblies for storing medication, coupled to the plurality of docking ports; one or more actuators; a gripping assembly, movable vertically by the one or more actuators to a proximate one or more of the medication container assemblies for picking a medication dosage out of the one or more of the medication container assemblies; and a receptacle carrier having a receptacle mount for holding one or more medication receptacles configured to receive the medication dosage.

30 Claims, 11 Drawing Sheets

Related U.S. Application Data application No. 16/379,831, filed on Apr. 10, 2019, now Pat. No. 10,614,916, and a continuation-in-part of application No. 16/430,456, filed on Jun. 4, 2019.

(56) References Cited

U.S. PATENT DOCUMENTS

| | | | |
|---|---|---|---|
| 6,006,946 A * | 12/1999 | Williams | B65G 1/045 221/2 |
| 6,529,801 B1 | 3/2003 | Rosenblum | |
| 7,698,019 B2 | 4/2010 | Moncrief et al. | |
| 8,027,849 B2 | 9/2011 | Johnson et al. | |
| 8,219,243 B2 | 7/2012 | Haas | |
| 8,280,550 B2 | 10/2012 | Levy et al. | |
| 8,521,327 B2 | 8/2013 | Pinney et al. | |
| 8,991,138 B2 | 3/2015 | Yuyama et al. | |
| 9,031,690 B2 | 5/2015 | Cotner | |
| 9,779,215 B2 | 10/2017 | Rosenblum | |
| 9,908,704 B2 | 3/2018 | Hawkes et al. | |
| 10,007,764 B2 | 6/2018 | Kim | |
| 10,049,188 B2 | 8/2018 | Iantorno et al. | |
| 10,614,916 B1 | 4/2020 | Einav et al. | |
| 2003/0024943 A1 | 2/2003 | MacDonald | |
| 2004/0155049 A1 | 8/2004 | Float et al. | |
| 2005/0259818 A1 | 11/2005 | Silverbrook et al. | |
| 2009/0321469 A1 * | 12/2009 | Knoth | B65B 5/103 221/7 |
| 2011/0017764 A1 * | 1/2011 | Liguori | G07F 11/165 221/1 |
| 2011/0315588 A1 | 12/2011 | Ross et al. | |
| 2012/0004770 A1 | 1/2012 | Ooyen et al. | |
| 2012/0187141 A1 | 7/2012 | Young et al. | |
| 2012/0209619 A1 | 8/2012 | Knotts et al. | |
| 2013/0123977 A1 | 5/2013 | Sanders et al. | |
| 2013/0240555 A1 | 9/2013 | Kim | |
| 2014/0262690 A1 | 9/2014 | Henderson et al. | |
| 2015/0081326 A1 | 3/2015 | Krishnapuram et al. | |
| 2015/0154709 A1 | 6/2015 | Cook | |
| 2016/0068328 A1 | 3/2016 | Lam et al. | |
| 2016/0132404 A1 | 5/2016 | Munson et al. | |
| 2017/0132867 A1 | 5/2017 | Berg et al. | |
| 2017/0267453 A1 | 9/2017 | Hellenbrand | |
| 2018/0122177 A1 | 5/2018 | Este et al. | |
| 2018/0357596 A1 | 12/2018 | Bedford | |
| 2020/0185076 A1 | 6/2020 | Einav et al. | |
| 2020/0327980 A1 | 10/2020 | Einav et al. | |
| 2020/0388100 A1 | 12/2020 | Einav et al. | |
| 2020/0388369 A1 | 12/2020 | Einav et al. | |

FOREIGN PATENT DOCUMENTS

| | | |
|---|---|---|
| WO | WO 2018/052160 | 3/2018 |
| WO | WO 2020/121165 | 6/2020 |
| WO | WO 2020/208439 | 10/2020 |
| WO | WO 2020/208477 | 10/2020 |
| WO | WO 2020/208479 | 10/2020 |
| WO | WO 2020/245739 | 12/2020 |

OTHER PUBLICATIONS

Final Official Action dated May 14, 2020 from the US Patent and Trademark Office Re. U.S. Appl. No. 16/214,081. (32 pages).
Applicant-Initiated Interview Summary dated Jul. 12, 2019 From the US Patent and Trademark Office Re. U.S. Appl. No. 16/379,831. (3 pages).
Notice of Allowance dated Nov. 19, 2019 From the US Patent and Trademark Office Re. U.S. Appl. No. 16/379,831. (3 pages).
Official Action dated Aug. 5, 2019 From the US Patent and Trademark Office Re. U.S. Appl. No. 16/379,831. (25 pages).
Official Action dated Sep. 9, 2019 From the US Patent and Trademark Office Re. U.S. Appl. No. 16/214,081. (33 pages).
Official Action dated May 15, 2019 From the US Patent and Trademark Office Re. U.S. Appl. No. 16/379,831. (24 pages).
Restriction Official Action dated Apr. 2, 2019 From the US Patent and Trademark Office Re. U.S. Appl. No. 16/214,081. (6 pages).
Interview summary dated Jul. 21, 2020 from the US Patent and Trademark Office Re. U.S. Appl. No. 16/430,456. (3 pages).
International Search Report and the Written Opinion dated Jun. 25, 2020 From the International Searching Authority Re. Application No. PCT/IB2020/052052. (10 Pages).
International Search Report and the Written Opinion dated Jun. 25, 2020 From the International Searching Authority Re. Application No. PCT/IB2020/053080. (13 Pages).
International Search Report and the Written Opinion dated Jun. 28, 2020 From the International Searching Authority Re. Application No. PCT/IB2020/053082. (13 Pages).
Official Action dated Jun. 25, 2020 from the US Patent and Trademark Office Re. U.S. Appl. No. 16/430,456. (15 pages).
Restriction Official Action dated Jul. 24, 2020 from the US Patent and Trademark Office Re. U.S. Appl. No. 16/379,835. (6 pages).
International Search Report and the Written Opinion dated Aug. 31, 2020 From the International Searching Authority Re. Application No. PCT/IB2020/055232.
Interview Summary dated Jan. 8, 2021 from the U.S. Appl. No. 16/379,835. (4 pages).
Official Action dated Nov. 25, 2020 From the U.S. Appl. No. 16/379,835. (38 Pages).

\* cited by examiner

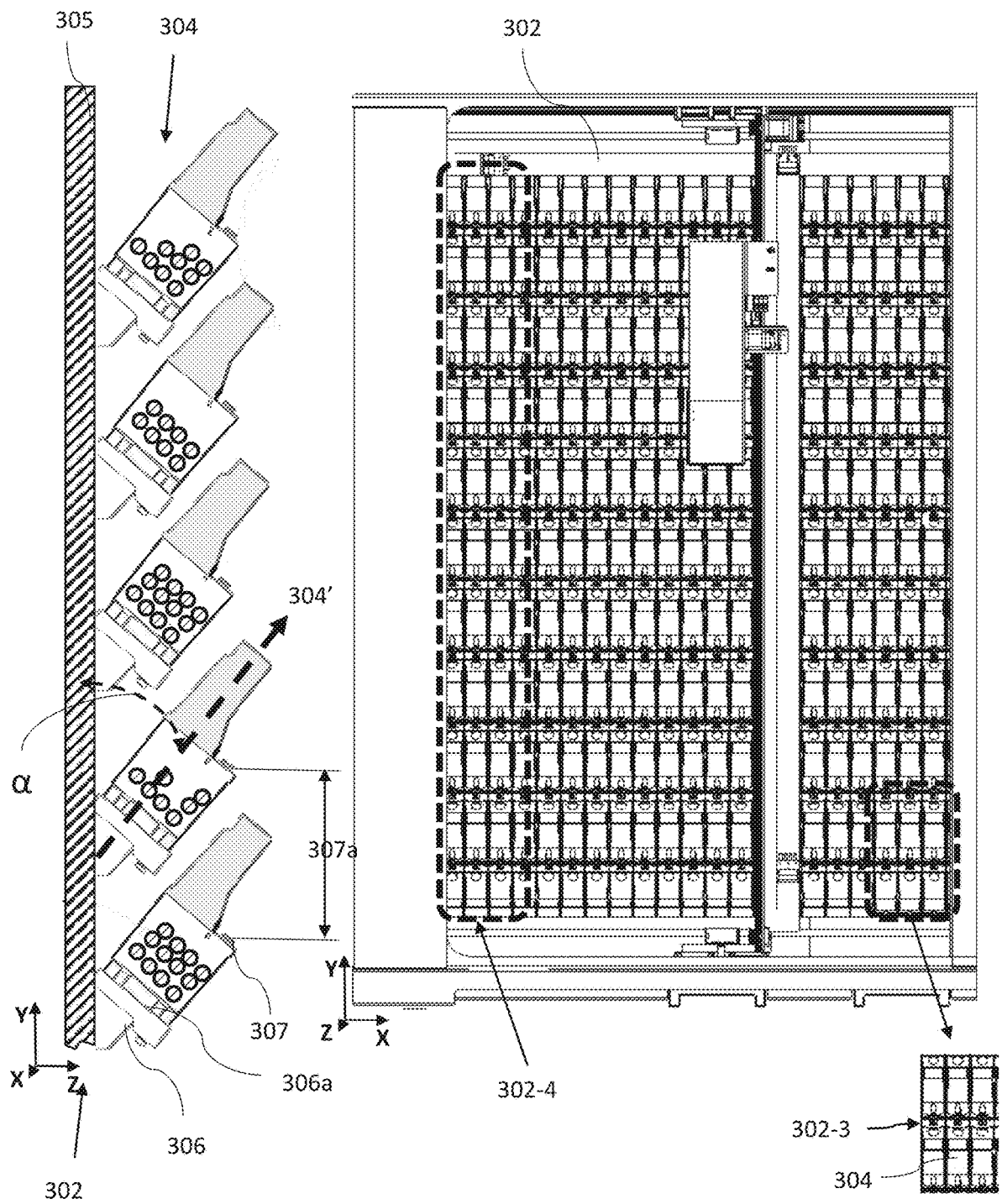

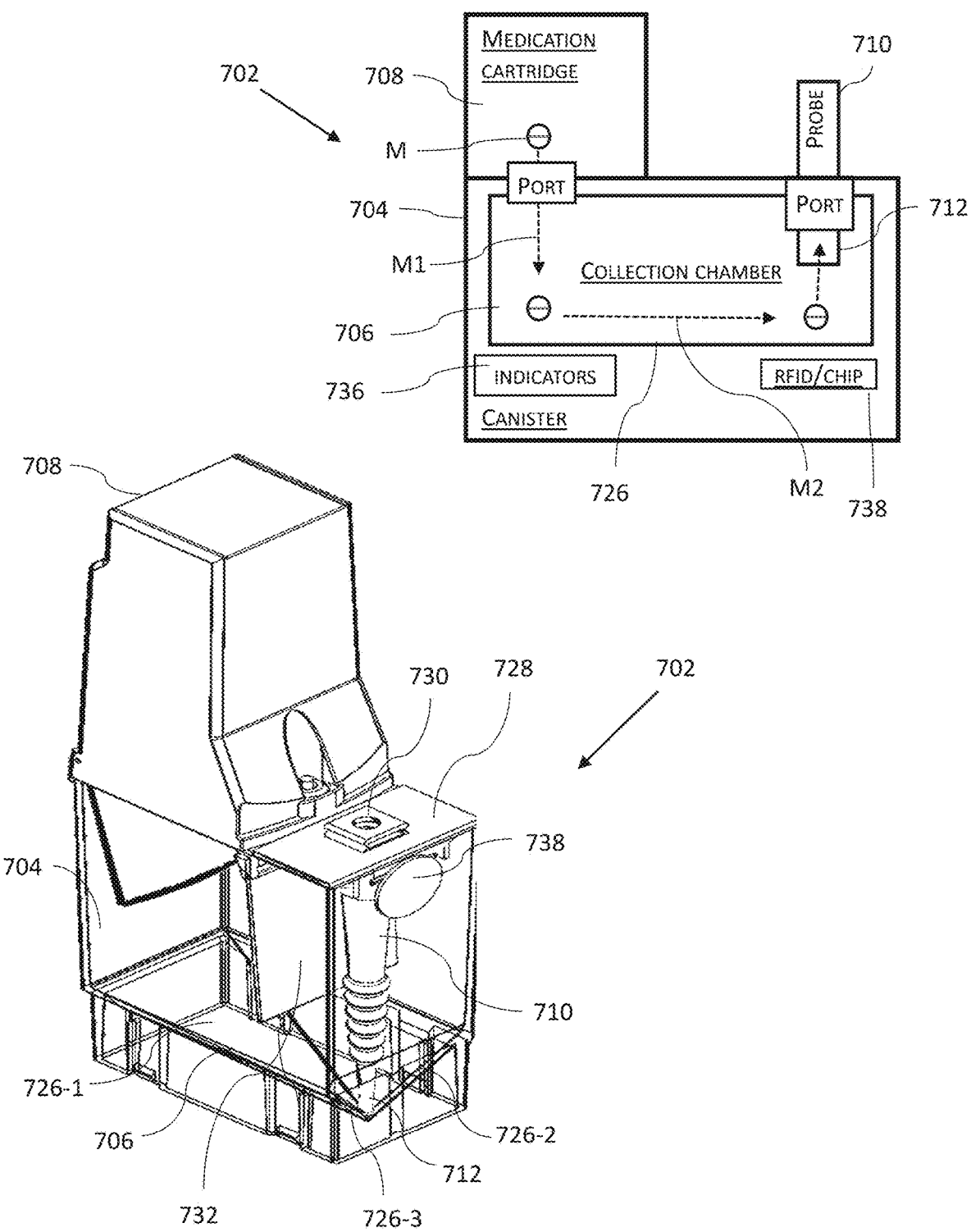

MEDICATION CONTAINERS IN MEDICATION DISPENSING SYSTEM

RELATED APPLICATIONS

This application is a Continuation-in-Part (CIP) of U.S. patent application Ser. Nos. 16/379,835 and 16/379,831, both filed on Apr. 10, 2019, and is also a Continuation-in-Part (CIP) of Ser. No. 16/430,456 filed on Jun. 4, 2019.

The contents of the above applications are all incorporated by reference as if fully set forth herein in their entirety.

FIELD AND BACKGROUND

The present invention, in some embodiments thereof, relates to a medication dispensing system and, more particularly, but not exclusively, to extracting medication out of medication containers and dispensing medication within medication receptacles.

US Patent Publication No. 2013/0123977 discloses "systems and methods for managing canisters used to automatically dispense medication. Canisters are configurable via a design process and a build process to accurately dispense a variety of medications. Design profiles are created and stored by a canister management system, and are federated to workstations used to build and fill the canisters, and to workstations used to dispense the medication. Information related to the build process, the fill process, and the dispense process is also federated by the system. The system also enables the transmission of other types of messages between client applications on the workstations and the canister management system. The system is useful to federate data regardless of a structure of a supply chain used to design, build, distribute, and use the canisters".

International Patent Publication No. WO 2018/052160 discloses "a medication dispenser having high space utilization, having a large quantity of medication packages loaded therein, having high medication-dispensing efficiency, and enabling smooth dispensing regardless of the size and type of the medication package. Provided is the medication dispenser comprising: a canister module in which a canister having the medication packages loaded therein is accommodated; and a pickup robot for picking up the medication packages in individual units, wherein the canister includes: L-shaped first and second walls for providing a loading space allowing the medication packages to move therein in the long axis direction of the canister; a guide for moving the first wall toward the second wall so as to adjust a gap with the second wall; a contact plate moving along the loading space, and bringing the medication packages into close contact with each other by pressure; and a spiral spring providing the pressure to the contact plate, having a strip shape, and wound in a coil shape".

US Patent Publication No. 2018/0122177 discloses "storage and distribution system for products in unit doses, including a plurality of housing units, each including a plurality of locations for products in unit doses. The housing units are organized on a vertical plane to produce at least one portion of a picking wall, in which the locations for products in unit doses face selective picking members. A picking unit includes picking members oriented on the picking wall for picking products packaged in unit doses. A collecting unit, arranged on a second side of the picking unit, includes a rack having a plurality of pegs facing towards the first side of the picking unit. The pegs are reached by the picking members so as to pick therefrom or deposit thereon products packaged in unit doses. The plurality of pegs as a whole can collect a smaller number of unit dose products than those that can be stored in the automatic store".

SUMMARY

The following describes some examples of embodiments of the invention. Some example of the invention are described herein and an embodiment may include features from more than one example and/or fewer than all features of an example.

According to an aspect of some embodiments of the present invention there is provided a medication dispensing system, comprising one or more medication panels, each having a plurality of docking ports located at a vertical displacement one from another. The medication dispensing system comprises: a plurality of medication container assemblies for storing medication, coupled to the plurality of docking ports; one or more actuators; a gripping assembly, movable vertically by the one or more actuators to a proximate one or more of the medication container assemblies for picking a medication dosage out of the one or more of the medication container assemblies; and a receptacle carrier having a receptacle mount for holding one or more medication receptacles configured to receive the medication dosage.

According to some embodiments of the invention, the plurality of medication container assemblies extend along a general container direction, which is transverse to a vertical plane in an acute angle.

According to some embodiments of the invention, the one or more medication panels comprise one or more port surfaces, and the plurality of docking ports are coupled to the port surfaces, and protrude in a general docking port direction, which is transverse to the one or more port surfaces in an acute angle.

According to some embodiments of the invention, the plurality of docking ports comprise a docking surface, which is transverse to a vertical plane in an acute angle.

According to some embodiments of the invention, the one or more medication panels are slanted in respect to a vertical plane.

According to some embodiments of the invention, the medication container assemblies are stationary in respect to the one or more medication panels, when coupled to the plurality of docking ports.

According to some embodiments of the invention, the receptacle carrier is movable vertically by the one or more actuator to approximate one or more of the medication container assemblies.

According to some embodiments of the invention, the medication container assemblies comprise a canister. The canister comprise a mounting rim, shaped and sized to couple the medication container assembly to one of the docking ports. The canister further comprise a medication collection chamber, having a guiding surface defining a portion of a bottom portion of the chamber. The medication container assemblies further comprise a cartridge for storing medication, coupled to the canister and having a medication release port. In some embodiments, the medication container assemblies comprise a gripping port to insert a probe for extracting the medication dosage. In some embodiments, the guiding surface is sloped from a point located underneath the medication release port to a point located underneath the gripping port.

According to some embodiments of the invention, the gripping assembly comprise a gripper platform, and a gripper. In some embodiments, the gripper is movably coupled to the gripper platform, to move the gripper in respect to the medication container assemblies. In some embodiments, the gripper is pivotally coupled to the gripper platform, to rotate the gripper in respect to the medication container assemblies.

According to some embodiments of the invention, one or more of the medication container assemblies is accessible by an operator while the gripping assembly is in motion. According to some embodiments of the invention, one or more of the medication container assemblies comprise electrical/electromagnetic circuit to transmit operational parameters of the medication container assemblies.

According to some embodiments of the invention, the vertically adjacent medication container assemblies have an overlap between a projection of a medication container assembly on a vertical plane, with a projection of another vertically adjacent medication container assembly on a vertical plane. In some embodiments, the overlap is greater than 10% of a projection of one or more of the vertically adjacent medication container assemblies on the vertical plane.

According to some embodiments of the invention, the receptacle carrier is coupled to the gripping assembly for holding one or more medication receptacles below the medication dosage. According to some embodiments of the invention, the receptacle carrier is coupled to the gripping assembly for holding one or more medication receptacles to have an overlap between a projection of a medication container assembly on a vertical plane, with a projection of the receptacle on a vertical plane, after the picking of the mediation dosage out of the medication container assembly.

According to an aspect of some embodiments of the present invention there is provided a method for dispensing medication dosage, by a system having medication container assemblies for storing medication. According to some embodiments, the method comprises: identifying a medication container assembly storing a selected medication, the medication container assembly is positioned in a vertical displacement to one or more medication container assemblies; approximating a gripping assembly to the medication container assembly by moving gripping assembly vertically towards the medication container assembly; manipulating the gripping assembly to extract medication dosage out of the medication container assembly; and dispensing dosage into one or more medication receptacles.

According to some embodiments of the invention, the method comprises moving the receptacle vertically to approximate the medication container assembly. According to some embodiments of the invention, the method comprises moving the receptacle vertically to approximate the gripping assembly. In some embodiments, the moving is prior to the dispensing. In some embodiments, the moving is prior to the manipulating.

According to some embodiments of the invention, the manipulating comprises: rotating at least a portion of the gripping assembly to be angular to a vertical plane; picking the medication dosage by a probe inserted within the medication container assembly; detaching the probe outside the medication container assembly; and positioning the dosage above an opening in the medication receptacle.

According to some embodiments of the invention, the method for dispensing medication dosage comprises manipulating a medication receptacle carrier to position the medication receptacle under the gripping assembly.

According to some embodiments of the invention, the approximating includes manipulating one or more medication receptacles together with the gripping assembly.

According to some embodiments of the invention, the time between the identifying and the dispensing is less than 1 sec.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as drug dispensing into medical receptacles, increasing dispensing speed, and reducing dispensing failures, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-3D are simplified schematic illustrations of a portion of a dispensing machine showing a perspective view, a front view, and a side view of a medication containers panel, according to some embodiments of the invention;

FIG. 7A-7B are simplified illustrations of a schematic view and a perspective view of a medication container assembly, according to some embodiments of the invention.

DESCRIPTION OF SPECIFIC EMBODIMENTS OF THE INVENTION

Figure 1:
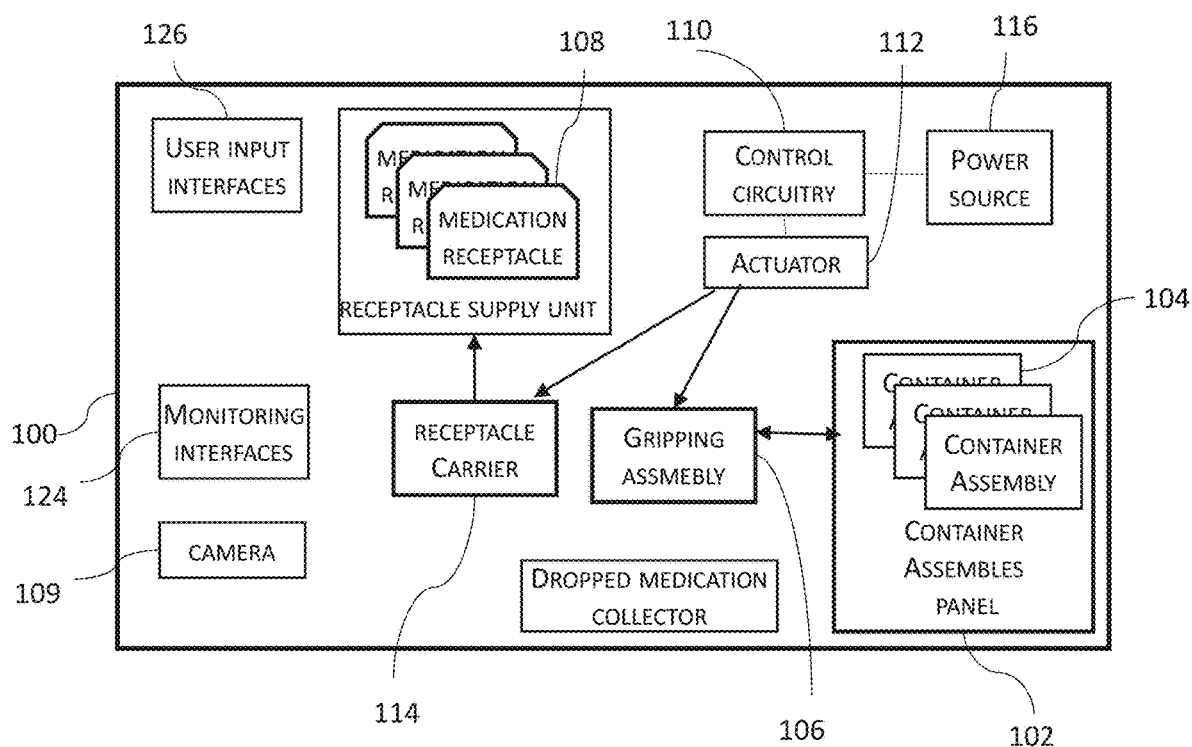
FIG. 1 is a simplified schematic illustration of a block diagram of a pharmaceutical dispensing system, according to some embodiments of the invention.

The present invention, in some embodiments thereof, relates to a medication dispensing system and, more particularly, but not exclusively, to extracting medication out of medication containers and dispensing medication within medication receptacles.

Overview

A broad aspect of some embodiments of the invention relates to an arrangement of assemblies within a medication dispensing system to affect operational parameters. Some examples of the operational parameters include: increasing dispensing rate, controlling vertical size, reducing horizontal size, increasing number of medication types available for dispensing, reducing mean time to repair, reducing mean time to prepare system, reducing mean time system accessed by, and reducing idle time.

According to some embodiments, the medication dispensing system has a gripping assembly that picks a medication dosage out of medication container assemblies arranged vertically on one or more medication panels, and dispenses the medication dosage into a medication receptacle. In some embodiments, the gripping assembly moves vertically between the container assemblies to approximate selected medication. In some embodiments, the receptacles move vertically to approximate medication container assemblies.

According to some embodiments, the vertical arrangement of the medication container assemblies allows positioning of both the gripping assembly and the receptacles nearby a medication container assembly during the dispensing process.

According to some embodiments, reducing the distance between the gripping assembly and the receptacles affect one or more of the operational parameters. In some embodiments, the operation parameter is affected by a minimal movement of a medication dosage, between extracting from a medication container assembly and disposing the dosage into a receptacle. In some embodiments, the gripping assembly and the receptacles are both coupled to a gripping assembly and move together. In some embodiments, the dispensing rate is affected by reducing movement of the gripping model in respect to the receptacle and/or vice versa.

According to some embodiments, there is no horizontal movements between the gripping assembly and the medication receptacles after taking a medication dosage. A potential advantage of reducing the horizontal movements is reducing the medication dispensing time to increase the medication packaging rate.

A broad aspect of some embodiments of the invention relates to the arrangement of assemblies of a medication dispensing system that affect usability.

According to some embodiments, the interior arrangement improves usability parameters related to system preparations, system operations, and/or system maintenance. In some embodiments, the interior arrangement affects the size of the system, which enable positioning the dispensing system closer to operators. In some embodiments, the interior arrangement improves the convenience of accessing the medication container assemblies. In some embodiments, the interior arrangement increases the dispensing rate and reduces wait time of a user for packaged medication.

An aspect of some embodiments of the invention relates to a medication dispensing system having medication container assemblies arranged vertically.

According to some embodiments, the dispensing system comprises one or more medication panels, and the medication container assemblies are disposed vertically on the panels. A potential advantage of having a medication panel extending vertically is reducing the horizontal sized of the panel. In some embodiments, reducing the horizontal sized of the panel reduces the horizontal size of the system.

According to some embodiments, the medication dispensing system has a gripping assembly configured to move vertically to a proximate one or more of medication container assemblies arranged vertically on a panel.

According to some embodiments, optimizing the arrangement of the medication container assemblies at the panels, reduces the travel trajectory of the gripping assembly. In some embodiments, optimizing the arrangement is in accordance to historical data of the gripping assembly movements and/or medication dispensed by the system, and/or a dispensing plan. In some embodiments, the location of the medication container assemblies is determined by data about the medication usage.

According to some embodiments, the gripping assembly has a portion configured to rotate between being positioned to pick a medication out of the medication container assembly, and being positioned above a receptacle for dispensing the medication dosage into the receptacle. A potential advantage is minimizing the time the container assembly is left open between holding a medication by the gripping assembly and releasing the medication dosage. In some embodiments, the time between the grabbing a medication dosage out of the medication container assembly and the dispensing of the medication dosage in a receptacle is shorter than 10 sec. Another potential advantage is reducing accidental loosing of the medication dosage from the gripping assembly prior to the dispensing of the medication dosage in a medication receptacle.

According to some embodiments, the medication container assemblies are slanted to a vertical plane. In some embodiments, positioning the medication container assemblies in a slanted orientation, improves the accessibility of a medication opening, used to extract medication out of the medication container assemblies. In some embodiments, positioning the medication container assemblies in a slanted orientation reduces at least some of the horizontal movements of the gripping assembly.

According to some embodiments, the gripping assembly is not actuated horizontally away from the container assembly between extracting the medication dosage from the container assembly and dispensing the medication dosage within the medication receptacle. In some embodiments, the maximal horizontal distance between the gripping assembly and the container assembly remains constant between extracting the medication dosage from the container assembly and dispensing the medication dosage within the medication receptacle. A potential advantage of reducing the maximal horizontal distance is reducing the horizontal size of the system.

An aspect of some embodiments of the invention relates to a medication dispensing system having medication container assemblies arranged vertically at a medication panel, and one or more of the container assemblies are accessible by an operator, without moving other container assemblies disposed at the panel.

According to some embodiments, the vertical arrangement of the medication container assemblies enable an ad-hoc access to a medication container assembly. In some embodiments, the access is possible during a dispensing operation. A potential advantage is enabling an un-scheduled access to the medication container assembly. Another potential advantage is reducing access restrictions to the medication containers, e.g. due to a requirement to idle the dispensing system.

An aspect of some embodiments of the invention relates to a medication dispensing system having medication container assemblies having a slanted medication-guiding surface.

According to some embodiments, the guiding surface directs a medication dosage within the container assembly towards a probe used for extracting a medication dosage out of the container. According to some embodiments, the container assemblies are disposed in a slanted orientation at the panel, so that the guiding surface is not horizontal and guiding the medication dosage is by the gravity force. A potential advantage is increasing the availability of medication dosage in proximity to the probe instead of accumulating away of the probe. A potential advantage is increasing the predictability of the percentage of medication extracted of the container assemblies.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Medication Dispensing System

Referring now to FIG. 1, which is a simplified schematic illustration of a block diagram of a pharmaceutical dispensing system, according to some embodiments of the invention.

As shown in FIG. 1, dispensing system 100 includes one or more medication panels 102 for accommodating medication supply. According to some embodiments, medication is stored in medication container assemblies 104. In some embodiments, medication container assemblies 104 are arranged vertically within medication panel 102. According to some embodiments, medication panels 102 have a plurality of docking ports for coupling medication container assemblies 104 to panels 102. In some embodiments, the docking ports are disposed vertically within medication panel 102.

According to some embodiments, dispensing system 100 includes a gripping assembly 106 configured to receive a medication dosage from medication containers 104 and to hold the medication dosage until disposing the medication dosage in a medication receptacle 108. According to some embodiments, gripping assembly 106 is configured to move next to panel 102 and to approximate a container assembly 104 for receiving a medication dosage.

In some embodiments, gripping assembly 106 does not move horizontally towards receptacle 108 after receiving the medication dosage. A potential advantage of reducing the horizontal movements is reducing the medication dispensing time to increase the medication packaging rate. Another potential advantage is reducing the risk of losing medication dosage from gripping assembly 106.

According to some embodiments, dispensing system 100 includes control circuitry 110 that outputs actuation signal to actuate gripping assembly 106. In some embodiments, system 100 actuates gripping assembly 106 using one or more actuators 112 receiving actuating signals from control circuitry 110.

As shown in FIG. 1, dispensing system 100 includes one or more receptacle carriers 114 for manipulating one or more medication receptacles 108 having an opening for receiving medication dosage. According to some embodiments, receptacle carrier 110 is movable independently of gripping assembly 106. In some embodiments, actuators 112 include one or more carrier actuators that move receptacle carrier 114. In some embodiments, carrier actuators move receptacle carrier 114 linearly. In some embodiments, carrier actuators move carrier 114 parallel to panel 102. In some embodiments, moving receptacle carrier 114 is synchronous with moving of gripping assembly 106.

Dispensing Process

Figure 2:
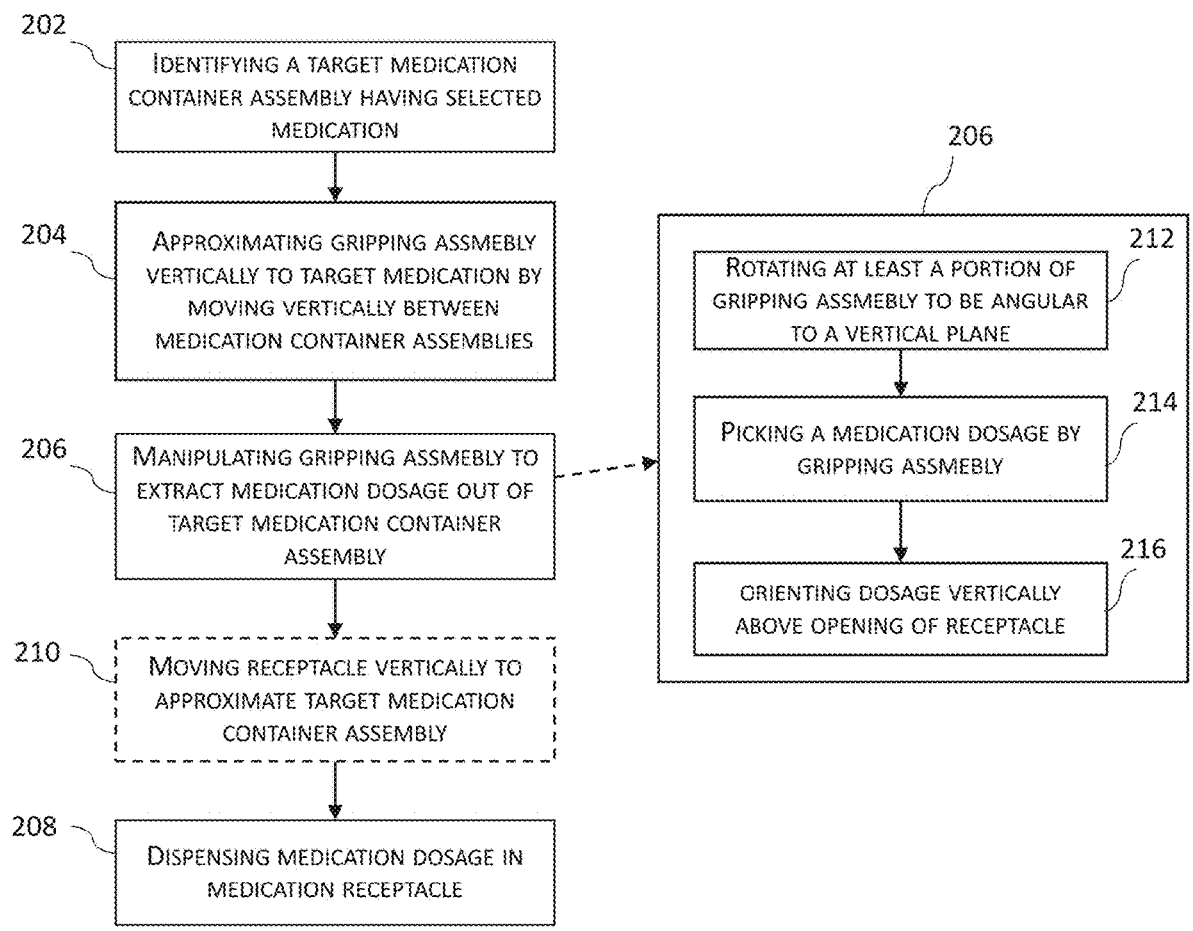
FIG. 2 is a simplified flowchart illustrating a dispensing process, according to some embodiments of the invention.

Referring now to FIG. 2, which is a simplified flowchart illustrating a dispensing process, according to some embodiments of the invention.

According to some embodiments, the dispensing process can be divided into the following categories of activities:

Pre-dispensing activities, such as: receiving data about selected medication to dispense, and preparing medication in medication container assemblies.

Dispensing activities, such as: identifying a target medication container assembly having the selected medication, extracting medication dosage, and dispensing medication in a receptacle. In some embodiments, the dispensing steps can be repeated, for example, when multiple dosages are dispensed in a single or multiple receptacles. In some embodiments, extracting the medication is by a gripping assembly positioned in proximity to the target medication container assembly.

Post-dispensing activities, such as: sealing the receptacles, putting target patient details on the receptacle, and placing the receptacles in a collection unit/medication tote.

As shown in FIG. 2, an example of dispensing activities include:

Identifying 202 a target medication container assembly having a selected medication. According to some embodiments, the target medication container assembly is positioned in a vertical displacement to one or more medication container assemblies.

Approximating 204 a gripping assembly to the target medication container assembly by moving gripping assembly vertically between medication container assemblies. According to some embodiments, approximating 204 is by a linear movement of the gripping assembly. In some embodiments, the linear movement is in a vertical direction. In some embodiments, approximating 204 is by a linear movement having horizontal and vertical movements. According to some embodiments, approximating 204 is by a control circuitry, outputting approximating signals to one or more actuators to move the gripping assembly.

Manipulating 206 the gripping assembly to extract medication dosage out of the target medication container assembly.

Dispensing 208 medication dosage in a medication receptacle. In some embodiments, there is no linear movement of the gripping assembly in a horizontal direction away of the target medication container assembly between manipulating 206 and dispensing 208.

According to some embodiments, the dispensing process include moving 210 receptacle vertically. In some embodiments, moving 210 is to approximate the target medication container assembly. In some embodiments, moving 210 is to approximate the gripping assembly. In some embodiments, moving 210 is prior to dispensing 208. In some embodiments, moving 210 is prior to manipulating 206. According to some embodiments, moving 210 is by a linear movement of the receptacle. In some embodiments, moving 210 is by a linear movement having horizontal and vertical movements. According to some embodiments, moving 210 is by a control circuitry, outputting signals to one or more actuators to move the receptacle.

According to some embodiments, manipulating 206 process include:

rotating 212 at least a portion of the gripping assembly to be angular to a vertical plane. According to some embodiments, rotating 212 include outputting rotation signals by control circuitry to one or more actuators to rotate the gripping assembly.

picking 214 the medication dosage by the gripping assembly. In some embodiments, picking 214 is by coupling the gripping assembly to a probe inserted within the target medication container assembly. In some embodiments, the probe is a portion of the gripping assembly. In some embodiments, picking 214 includes detaching the probe outside the medication container assembly.

According to some embodiments, picking 214 include outputting dosage manipulation signals by control circuitry to one or more actuators to move the gripping assembly to manipulate the medication dosage out of the medication container assembly.

orienting 216 the medication dosage above an opening the medication receptacle. In some embodiments, orienting 216 include rotating the gripping assembly. In some embodiments, orienting 216 include rotating the gripping assembly in a direction opposite to rotating 212. In some embodiments, orienting 216 include orienting a probe detached from the medication container assembly. In some embodiments, the maximal horizontal distance between the gripping assembly and the target medication container assembly does not change during orienting 216.

According to some embodiments, the time between approximating 204 and dispensing 210 is less than 5 sec. In some embodiments, the time between approximating 204 and dispensing 210 is less than 3 sec. In some embodiments, the time between approximating 204 and dispensing 210 is less than 1 sec.

Medication Panel

Referring now to FIGS. 3A-3D which are simplified schematic illustrations of a portion of a dispensing machine showing a perspective view, a front view, and a side view of a medication containers panel, according to some embodiments of the invention.

Dispensing system 300, has a medication panel 302 that accommodates a plurality of medication container assemblies 304, and the medication container assemblies 304 are arranged vertically.

According to some embodiments, two or more medication containers assemblies 304 are in a vertical layout when two or more medication containers assemblies 304 are positioned one vertically above another. In some embodiments, medication containers assemblies 304 are in a vertical layout when there is a vertical distance between the lowest points of adjacent medication containers assemblies 304.

Figure 3A:
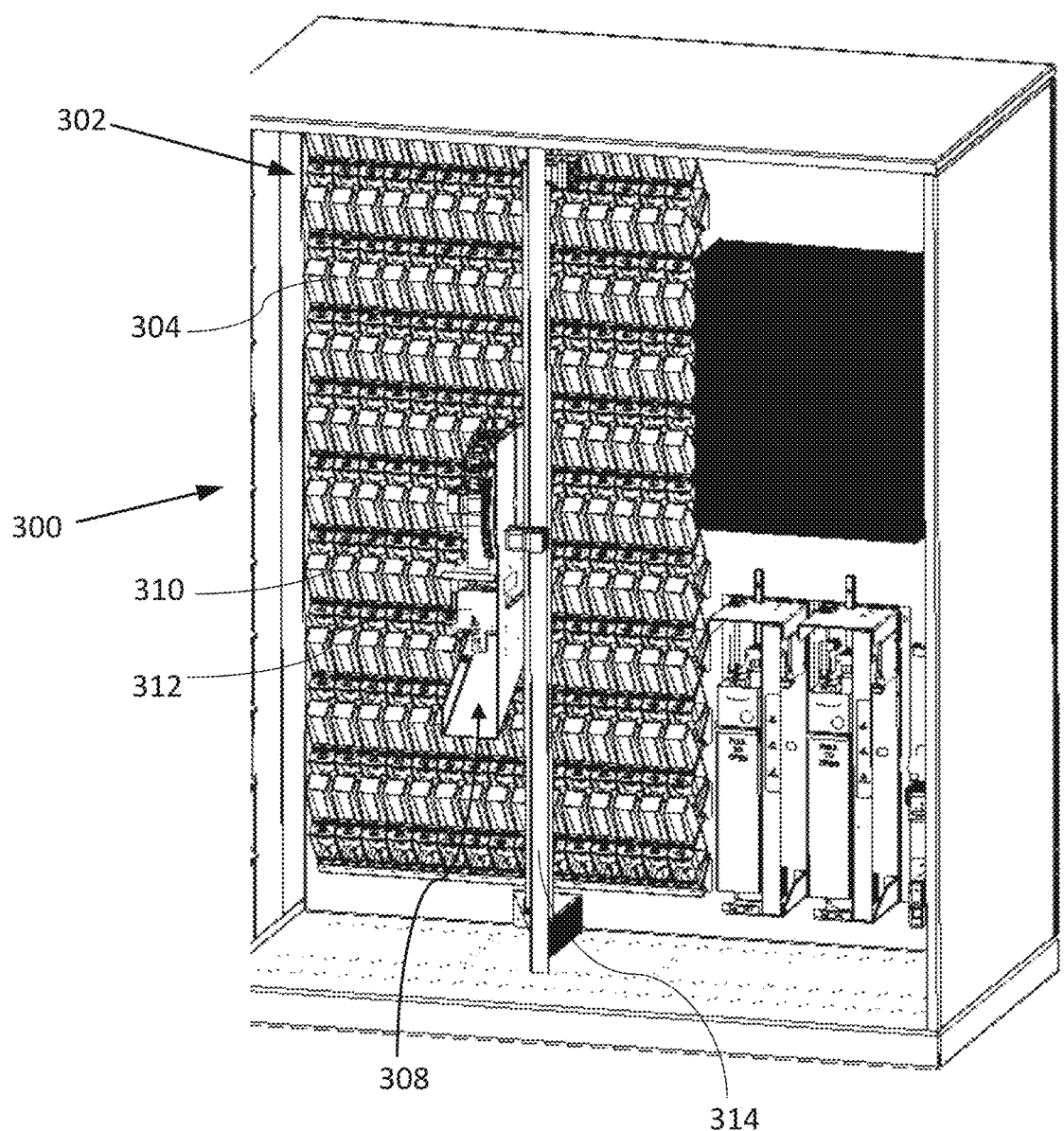
Figure 3B:
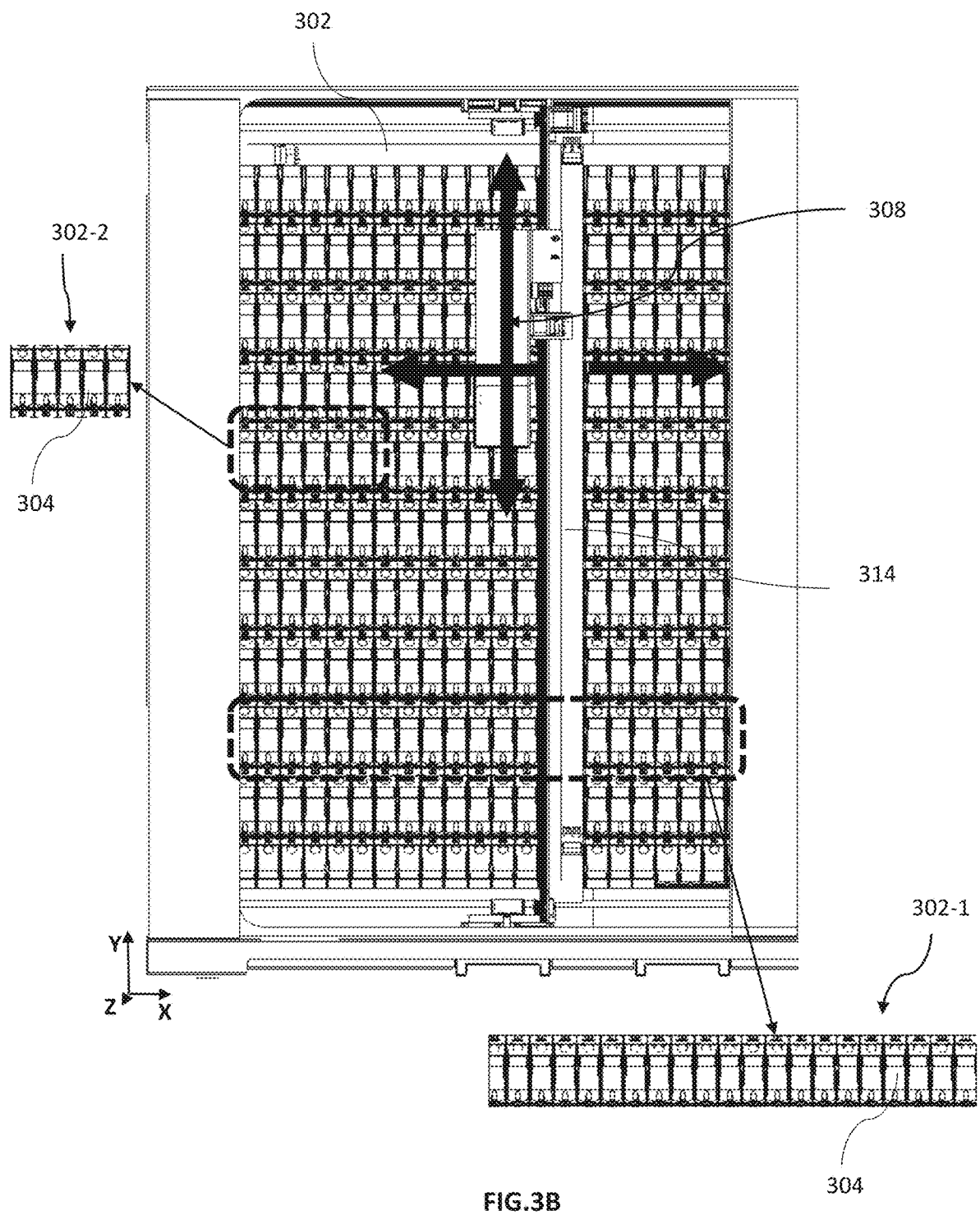

As shown in the example embodiment of FIGS. 3A-3B, panel 302 is vertically flat. In some embodiments, panel 302 is defined as a vertical panel when the height of panel 302 is bigger than its maximal horizontal width. In some embodiments, panel 302 is defined as a vertical panel when the height of panel 302 is at least 1.5 times bigger than its maximal horizontal width.

A potential advantage of having a vertical panel is reducing the horizontal size of the panel. In some embodiments, reducing the horizontal size of the panel reduces the horizontal size of the dispensing system at least in one direction.

According to some embodiments, panel 302 is configured to hold between 10 and 500 medication container assemblies 304. In some embodiments, panel 302 is configured to hold between 30 and 400 medication container assemblies 304. In some embodiments, panel 302 is configured to hold between 100 and 300 medication container assemblies 304. According to some embodiments, panel 302 is configured to hold medication container assemblies 304 in a matrix having between 2 and 100 rows. In some embodiments, panel 302 is configured to hold medication container assemblies 304 in a matrix having between 5 and 50 rows. In some embodiments, panel 302 is configured to hold medication container assemblies 304 in a matrix having between 10 to 30 rows.

According to some embodiments, medication panel 302 is formed of a plurality of sub-panels 302-1/302-2. In some embodiments (as shown for example in FIG. 3B), sub-panels 302-1/302-2 have a horizontal layout. In some embodiments, sub-panels 302-1 are sized to form a row of panel 302. In some embodiments, a row of panel 302 is formed of a plurality of sub-panels 302-2. In some embodiments (as shown for example in FIG. 3C), sub-panels 302-3/302-4 have a vertical layout.

Slanted Medication Containers

According to some embodiments, as shown for example in FIG. 3D, medication container assemblies 304 have a slanted orientation with a vertical plane, when coupled to panel 302. In some embodiments, medication container assemblies 304 coupled to panel 302 extend in a direction 304', which is angular to a vertical plane in an acute angle $\alpha$. A potential advantage of disposing container assemblies 304 in a slanted orientation is increasing density of container assemblies 304 on panel 302 (increase the number of container assemblies 304 per panel 302 height).

In some embodiments, the angle $\alpha$ is between about 10 and about 90 degrees. Optionally, the angle $\alpha$ is between about 15 degrees and about 60 degrees. Optionally, the angle $\alpha$ is between about 20 degrees and about 45 degrees.

According to some embodiments, two vertically adjacent medication container assemblies 304, have an overlap between the projection of one medication container assembly 304 on a vertical plane (e.g. in direction X-Y), with the projection of a vertically adjacent medication container assembly 304 on a vertical plane (e.g. in direction X-Y). In some embodiments, the overlap between the projections is greater than 10% of a projection of one or more of the vertically adjacent medication container assemblies 304 on the vertical plane. According to some embodiments, two vertically adjacent slanted medication container assemblies 304, have an overlap between a projection of an upper portion of one medication container assembly 304 on a vertical plane (e.g. in direction X-Y), with a projection of a bottom portion of a vertically adjacent medication container assembly 304 on a vertical plane. In some embodiments, the overlap between the projections is greater than 10% of a projection of one or more of the upper portion or the bottom portion of the adjacent medication container assemblies 304 on the vertical plane.

A potential advantage of having a vertical overlap is reducing a dead area between medication containers assemblies 304 in a vertical direction (Y). Some examples of potential benefits of reducing the dead area are: increasing the density of medication containers assemblies 304 on panel 302 in a vertical direction, increasing the density of medications provided by containers assemblies 304 on panel 302 in a vertical direction, reducing a vertical size of panel 302 in a vertical direction, and increasing the potential number of containers assemblies 304 in system 300.

According to some embodiments, two vertically adjacent medication container assemblies 304, have an overlap between the projection of one medication container assembly 304 on a horizontal plane (e.g. in direction X-Z), with the projection of a vertically adjacent medication container assembly 304 on a horizontal plane (e.g. in direction X-Z). In some embodiments, the overlap between the projections is greater than 10% of a projection of one or more of the vertically adjacent medication container assemblies 304 on the horizontal plane. According to some embodiments, two vertically adjacent slanted medication container assemblies 304, have an overlap between a projection of an upper portion of one medication container assembly 304 on a horizontal plane (e.g. in direction X-Z), with a projection of a bottom portion of a vertically adjacent medication container assembly 304 on a horizontal plane (e.g. in direction X-Z). In some embodiments, the overlap between the projections is greater than 10%.

A potential advantage of having a horizontal overlap is reducing a dead area between medication containers assemblies 304 in a horizontal direction (e.g. Z). Some examples of potential benefits of reducing the dead area are: increasing the density of medication containers assemblies 304 of on panel 302 in a horizontal direction (e.g. Z), increasing the density of medications provided by containers assemblies 304 on panel 302 in a horizontal direction, reducing the horizontal size of panel 302, and increasing the potential number of containers assemblies 304 in system 300.

According to some embodiments, medication panel 302 include a panel base 305 and a plurality of docking ports 306 are coupled to panel base 305, and medication container assemblies 304 are coupled to panel 302 by connecting medication container assemblies 304 to docking ports 306.

According to some embodiments, panel base 305 is vertically slanted, angular to a vertical plane. In some embodiments, panel base 305 has an arcuate layout, having an arcuate cross section extending vertically. Optionally, panel base 305 has a cylindrical layout having a cylindrical cross section extending vertically. Optionally, panel base 305 has a polygonal layout having a polygonal or an unclosed polygonal cross section extending vertically.

According to some embodiments, medication container assemblies 304 are stationary in respect to medication panel 302, when coupled to panel 302.

According to some embodiments, medication containers assemblies 304 have a medication port 307. In some embodiments, two or more medication containers assemblies 304 are define as being in a vertical layout when two or more medication ports 307 of the two or more medication containers assemblies 304 are positioned one above another. In some embodiments, two or more medication containers assemblies 304 are in a vertical layout when there is a vertical distance 307a between the projection of the lowest points of two or more of ports 307 on a vertical plane. In some embodiments, the vertical distance 307a is between 2 cm and 40 cm. In some embodiments, the vertical distance 307a is between 5 cm and 30 cm. In some embodiments, the vertical distance 307a is between 7 cm and 20 cm. In some embodiments, the vertical distance 307a is between 0.5 and 5 times the maximal length medication containers assemblies 304. In some embodiments, the vertical distance 307a is between 0.5 and 1 times the maximal length medication containers assemblies 304. In some embodiments, the vertical distance 307a is between 1 and 1.5 times the maximal length medication containers assemblies 304.

According to some embodiments, docking ports 306 are shaped to extend in a general port direction transverse to panel base 305. In some embodiments, docking ports 306 have a docking surface 306a angular to panel base 305, so that medication container assemblies 304 coupled to docking surface 306a are angular to a vertical plane. In some embodiments, docking surface 306a are angular to panel base 305, so that medication container assemblies 304 coupled to docking surface 306a are angular to panel base 305.

According to some embodiments, as shown for example in FIG. 3A, dispensing machine has a gripping assembly 308, which holds gripping assembly 308. In some embodiments, gripping assembly 308 holds receptacle carrier 312. In some embodiments, gripping assembly 308 is a robotic arm that moves gripping assembly 308 vertically next to medication container assemblies 304.

According to some embodiments, dispensing machine 300 includes a vertical rail 314 movable next to panel 302. In some embodiments, rail 314 is movable horizontally. According to some embodiments, gripping assembly 308 is moveably mounted on rail 314. In some embodiments, gripping assembly 308 is configured to move vertically next to panel 302 by sliding head 308 on rail 314. In some embodiments, gripping assembly 308 is configured to move horizontally next to panel 302 by moving rail 314 in a horizontal direction. In some embodiments, rail 314 is coupled to one or more horizontal rails. According to some embodiments (not shown), gripping assembly 308 is moveable on a horizontal rail coupled to medication panel 302, and the linear movement of head 308 is on the horizontal rail. In some embodiments, a vertical movement of gripping assembly 308 is by moving a horizontal rail on one or more vertical rails provided at medication panel 302.

According to some embodiments, the dispensing machine includes a plurality of abutting medication panels. Optionally, the dispensing machine includes a plurality of non-abutting medication panels. In some embodiments, the plurality of medication panels are positioned vertical to each other. In some embodiments, the plurality of vertical panels are positioned horizontal to each other. According to some embodiments, a plurality of medication panels are disposed at the same side/zone of the dispensing machine. In some embodiments, a plurality of medication panels are disposed at difference sides/zones of the dispensing machine. In some embodiments, the dispensing machine includes medication planes having different geometries/layouts.

Figure 4:
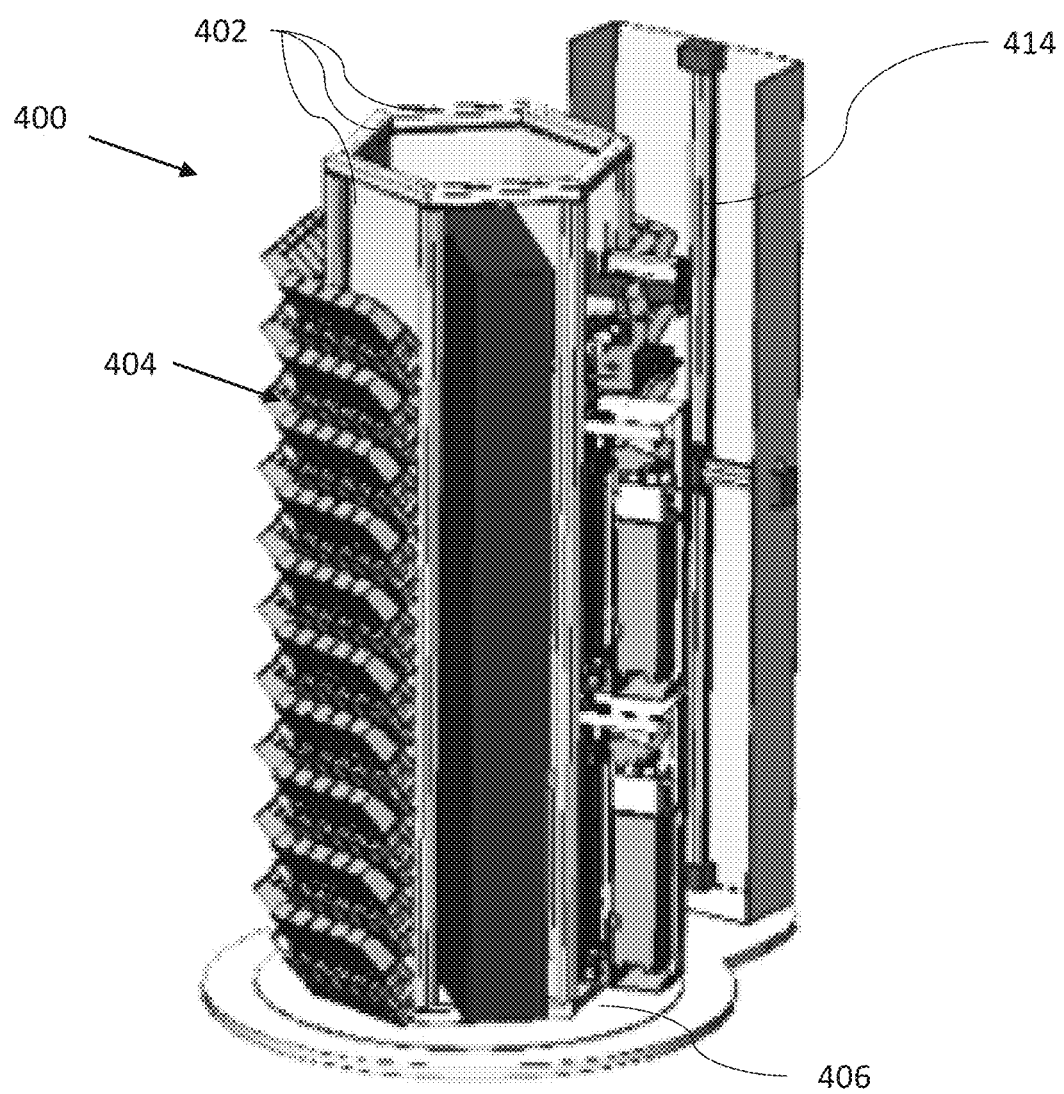
FIG. 4 is a simplified illustration of a portion of a dispensing machine showing a perspective view of a medication containers panel, according to some embodiments of the invention.

Referring now to FIG. 4, which is a simplified illustration of a portion of a dispensing machine showing a perspective view of a medication containers panel, according to some embodiments of the invention.

Dispensing system 400, has a plurality of medication panels 402 positioned next to each other, each accommodating a plurality of medication container assemblies 404, and the medication container assemblies 404 are arranged vertically. According to some embodiments, the gripping assembly (not shown) is movable vertically next to panel 402. In some embodiments, the gripping assembly is coupled to rail 414. According to some embodiments, dispensing machine 400 has a panel base 406. In some embodiments, panels 402 are coupled to base 406. In some embodiments, one or more of panels 402 are pivotally connected to base 406 and rotatable along a vertical axis. In some embodiments, gripping head approximates medication container assemblies 404 by rotating panels 402 along vertical axis. Optionally, panels 402 are coupled to base 406, which is rotatable about a vertical axis.

A potential advantage of arranging a plurality of panels in a cylindrical/curved/polygonal/semi-polygonal layout, as shown for example in FIG. 4, is a reduction in the horizontal space occupied by the panels. Another potential advantage of approximating gripping assembly to medication container assemblies 404 by a rotational movement is reducing horizontal movements, e.g. this may eliminate the need of horizontal rails.

A potential advantage of having a plurality of panels, is providing an operator a safe access to panels which are away of gripping assembly. Another potential advantage is having panels accessible to an operator without idling the dispensing machine.

Gripping Assembly

Figure 5:
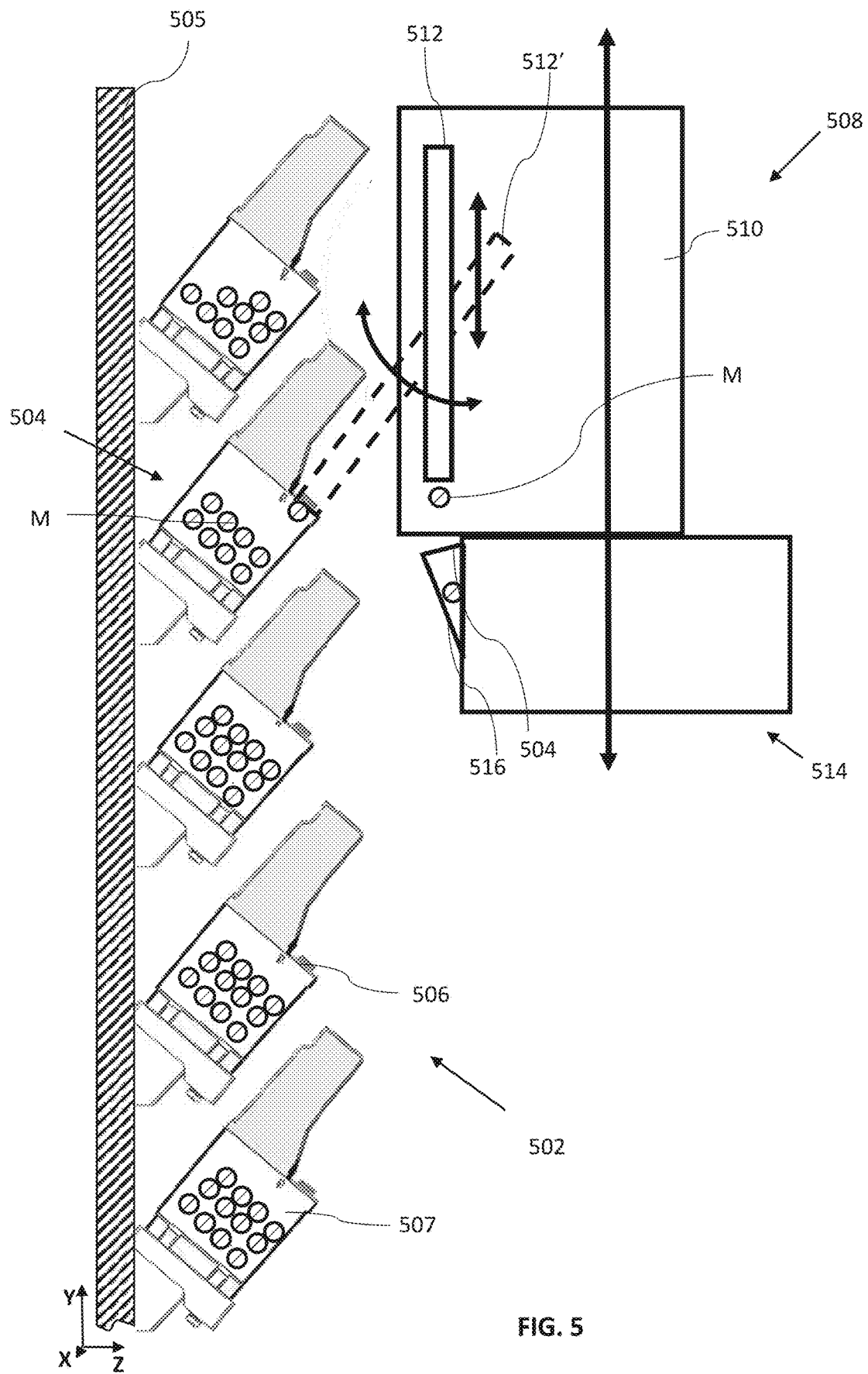
FIG. 5 is a simplified schematic illustration of a portion of a dispensing machine showing a side view of a medication containers panel, according to some embodiments of the invention.

Referring now to FIG. 5, which is a simplified schematic illustration of a portion of a dispensing machine showing a side view of a medication containers panel, according to some embodiments of the invention.

According to some embodiments, as shown in the example embodiment of FIG. 5, dispensing machine 500 includes a medication panel 502, and medication containers assemblies 504 coupled in a vertical layout at medication panel 502. Medication containers assemblies 504 accommodate medication M and have a medication port 506. According to some embodiments, medication M is in the form of medication pills. In some embodiments, is in the form of powder. In some embodiments, medication M is in the form of fluid. In some embodiments, containers assemblies 504 at panel 502 accommodate medication M of the same form. In some embodiments, containers assemblies 504 at panel 502 accommodate medication M is a variety of forms.

In some embodiments, medication dosage is extracted out of medication containers assemblies 504 via medication port 506. According to some embodiments, dispensing machine 500 has a gripping assembly 508 vertically movable next to medication containers assemblies 504, between medication containers assemblies 504. Gripping assembly 508 includes a gripper platform 510 and a gripper 512 movably coupled to gripper platform 510. In some embodiments, gripper 512 is movable to approximate medication port 506 to pick medication M. In some embodiments, gripper 512 is rotatable about a horizontal axis to approximate medication port 506. In some embodiments, gripper 512 is linearly movable to approximate medication port 506.

According to some embodiments, dispensing machine 500 includes a receptacle carrier 514 for manipulating one or more medication receptacles 516. In some embodiments, as shown for example in FIG. 5, receptacle carrier 514 is coupled to gripping assembly 508. In some embodiments, when receptacle carrier 514 is coupled to gripping assembly 508, receptacles are held in proximity to a tip of gripper 512.

According to some embodiments, gripper 512 is a probe gripper, configured to pick a probe to hold medication dosage. In some embodiments, gripper 512 is configured to apply suction in a probe to pick and hold medication M by the probe.

In some embodiments, gripper 512 is configured to grab a probe inserted in a medication container by approximating gripper 512 to the probe for grabbing the probe away of the medication container assembly 504 by a linear motion. In some embodiments, gripper 512 is configured to return the probe to the container by a linear motion towards of medication container assembly 504. In some embodiments, gripper 512 is actuated to move linearly by a linear system coupled to platform 510. In some embodiments, moving gripper 512 in linear motion is without moving platform 510 in respect to medications panel 502.

According to some embodiments, a picked probe is rotated by gripper 512 to be positioned above medication receptacle 516 for dispensing extracted medication dosage M into medication receptacle 516. In some embodiments, gripper 512 is rotationally coupled to platform 510. In some embodiments, rotating of gripper 512 is by rotation system 514 coupled to platform 510. In some embodiments, head 500 is configured to move the gripper 512 in a rotational motion without moving platform 510 in respect to medication panel 510. In some embodiments, there is no linear movement of gripper 512 in a horizontal direction away of container assembly 504 between the extracting and the dispensing of medication dosage M. In some embodiments, the rotation is in the range of 5 to 85 deg. In some embodiments, the rotation is in the range of 10 to 60 deg. In some embodiments, the rotation is in the range of 20 to 45 deg.

A potential advantage of reducing linear movements of gripper assembly 508 is reducing dispensing time. A potential advantage of coupling gripper assembly 508 and receptacle carrier 514 and reducing linear movements between them is reducing dispensing time. In some embodiments, the time between grabbing of the probe out of container assembly 504 by gripper 512 and dispensing medication dosage M in the medication receptacle 516 is shorter than 5 sec. In some embodiments, the time between grabbing of a probe out of container assembly 504 by gripper 512 and dispensing medication dosage M in medication receptacle 516 is shorter than 2 sec. In some embodiments, the time between grabbing of a probe out of container assembly 504 by gripper 512 and dispensing medication dosage M in medication receptacle 516 is shorter than 0.5 sec.

According to some embodiments, there is an overlap between the projection of at least of some of medications M stored in one assembly 504 on a horizontal plane (in direction X-Z), with the projection of at least of some of medications M stored in a vertically adjacent assembly 504 on a horizontal plane (in direction X-Z). In some embodiments, the overlap between the projections on the medications M is greater than 10%. According to some embodiments, there is an overlap between the projection of at least of some of medications M stored in one assembly 504 on a vertical plane (in direction X-Y), with the projection of at least of some of medications M stored in a vertically adjacent assembly 504 on a vertical plane (in direction X-Y). In some embodiments, the overlap between the projections on the medications M is greater than 10%.

Referring now to FIGS. 6A-6D, which are simplified schematic illustrations of a portion of a dispensing machine showing side views of a medication panel, according to some embodiments of the invention.

Dispensing machine 600 is similar to dispensing machine 500 described elsewhere herein. Machine 600 has a plurality of medication containers assemblies 604 disposed in a vertical layout (having medication containers assemblies 604 above each other in vertical direction Y) on panel 602. Gripping assembly 606 is configured to move across panel 604, and approximate medication containers assemblies 604. Gripping assembly 606 is configured to move between medication containers assemblies 604 by a linear movement in a vertical direction Y. In some embodiments, the linear movement is a combination of horizontal movements in direction X and vertical movement in direction Y across panel 602. In some embodiments, gripping assembly has a gripper 608 configured to manipulate medication dosage M between medication containers assemblies 604 and dispensing into a medication receptacle.

Dispensing machine 600 has receptacle carrier 610 for manipulating one or more medication receptacles 612. In some embodiments, medication receptacles 612 are medication envelopes. Receptacle carrier 610, is holding receptacles 612 vertically under gripper 608. In some embodiments, when a probe P is used to hold medication dosage M, receptacle carrier 610, is holding receptacle 612 vertically under the tip of the probe P, such as a medication disposed at the tip of the probe is dispensed by dropping the medication M from the probe P into the opening of receptacle 612.

Figures 6A, 6B:
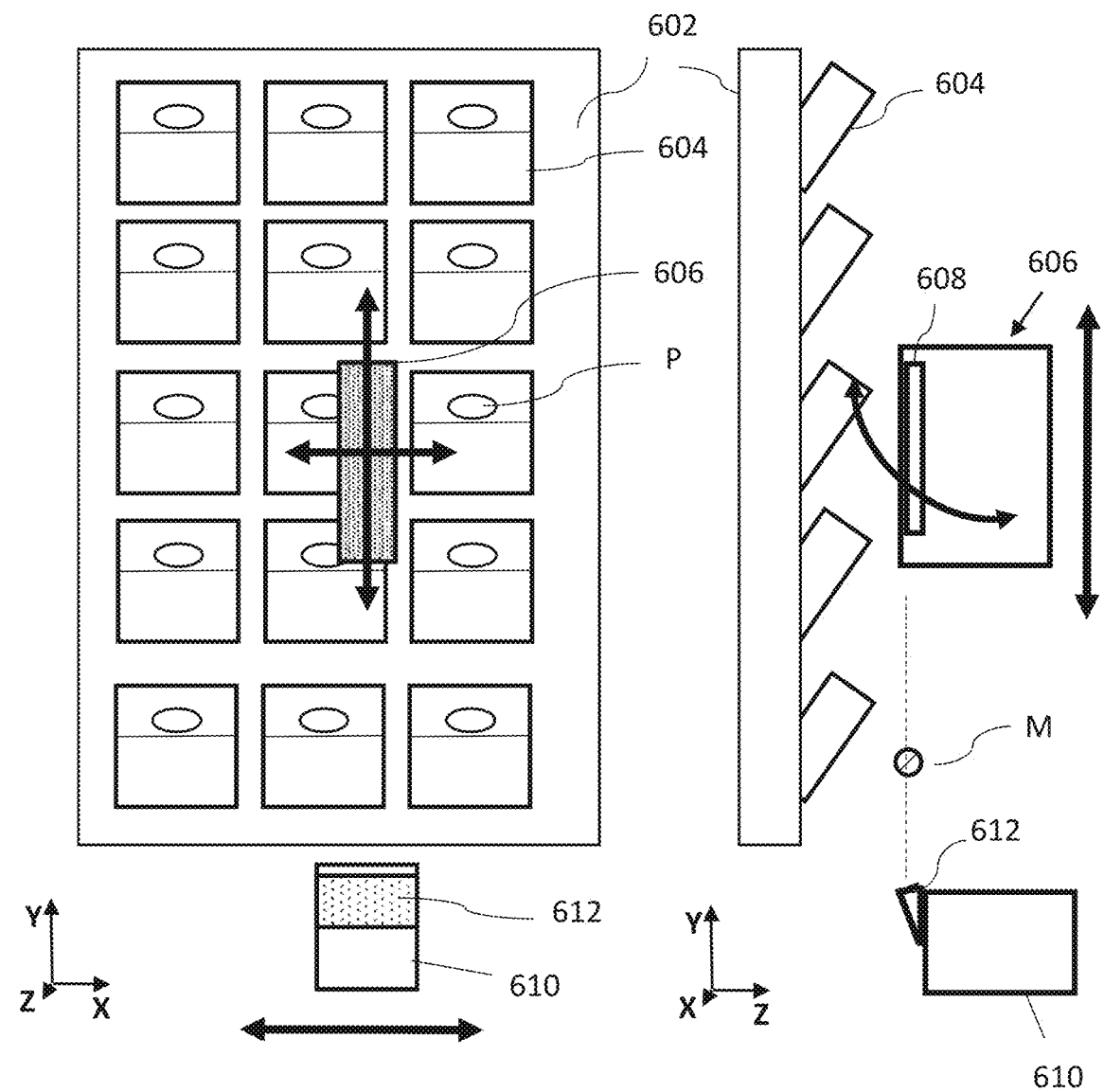
FIGS. 6A-6C are simplified schematic illustrations of a portion of a dispensing machine, showing side views of a medication panel, according to some embodiments of the invention.

In the example embodiment shown in FIGS. 6A-6B, dispensing machine 600 has receptacle carrier 610 decoupled of gripping assembly 606. According to some embodiments, one or more carrier actuators move receptacle carrier 610 horizontally. In some embodiments, receptacle carrier 610 manipulates receptacle in horizontal direction X below medication containers assemblies 604. In some embodiments, moving horizontally, is to maintain a maximal horizontal distance D1 between gripper 608 and an opening of receptacle 612 within a pre-define range. In some embodiments, distance D1 is shorter than 50 cm. In some embodiments, distance D1 is shorter than 10 cm. In some embodiments, distance D1 is shorter than 20 cm. In some embodiments, distance D1 is shorter than 5 cm.

In some embodiments, for example as shown in FIG. 6A, controlling the distance D1 is by moving both gripping assembly 606 and carrier 610 in a horizontal direction (e.g. direction X).

According to some embodiments, moving carrier 610 to position carrier 610 at a horizontal distance from gripper 608 is prior to approximating container assembly 604. In some embodiments, moving carrier 610 to position carrier 610 at a pre-defined horizontal distance from gripper 608 is after gripping assembly 606 receives a medication dosage M and prior to dispensing it into receptacle 610.

According to some embodiments, receptacle carrier 610 is movable vertically in direction Y. In some embodiments, a vertical carrier actuator, moves carrier 610 vertically.

Figure 6C:
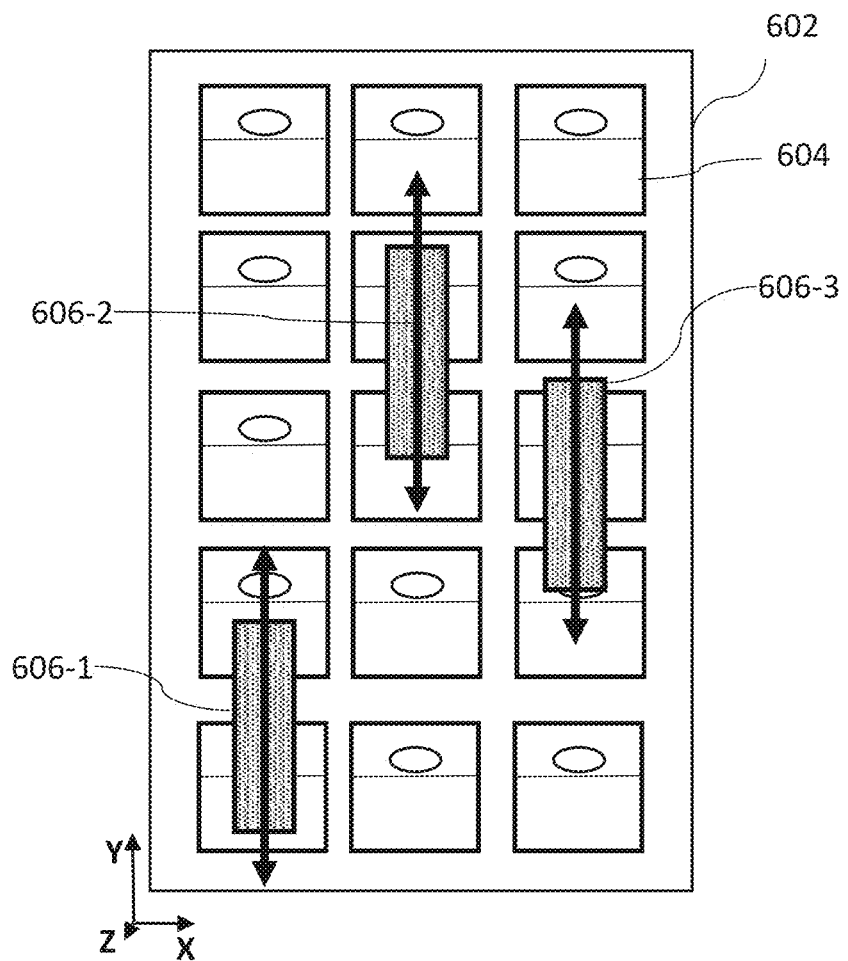

According to some embodiments, as shown for example in FIG. 6C, panel 602 can have a plurality of gripping assemblies 606. In some embodiments, gripping assemblies 606-1 to 606-3 are designated to approximate one or more rows of medication container assemblies 604 positioned in a column of container assemblies 604. In some embodiments, gripping assemblies 606-1 to 606-3 are configured to move only in a vertical direction, without having a horizontal movement between columns of container assemblies 604. In some embodiments, actuating gripping assemblies 606-1 to 606-3 is simultaneous without a dependency between them. In some embodiments, not having a horizontal movement between columns reduces the complexity of dispensing machine 600, for example components required for horizontal actuation of gripping assemblies. A potential advantage of having multiple gripping assemblies is having a safe access to container assemblies 604, which are coupled on columns, which do not have gripping assembly active in a dispensing process.

According to some embodiments (not shown), dispensing machine 600 has a plurality of gripping assemblies 606 designated to move horizontally between one or more columns of medication container assemblies 604. In some embodiments, gripping assemblies 606 are configured to move only in a horizontal direction, without having a vertical movement between rows of container assemblies 604. In some embodiments, gripping assemblies 606-1 to 606-3 are actuated simultaneously without a dependency between them.

Figure 6D:
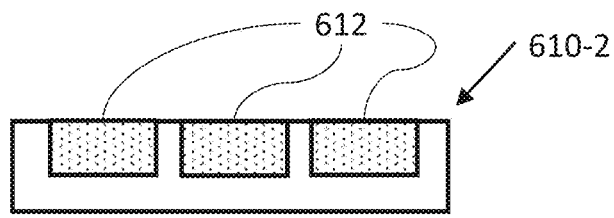
FIG. 6D is a simplified schematic illustration of a portion of a dispensing machine showing side views of a receptacle carrier, according to some embodiments of the invention

According to some embodiments, as shown for example in FIG. 6D, receptacle carrier 610-2 is configured to hold a plurality of receptacles 612. In some embodiments, carrier 610-2 does not assume horizontal movements between columns of container assemblies 604. In some embodiments, not having a horizontal movement between columns reduces the complexity of dispensing machine 600, for example components required for horizontal actuation of carrier 610-2. In some embodiments, carrier 610-2 is configured to be actuated to have vertical movements without having horizontal movements. In some embodiments, carrier 610-2 is stationary to position receptacles 612 below gripping assemblies 606. In some embodiments, carrier 610-2 is stationary between extracting medication dosage M and dispensing medication dosage M in receptacles 612.

Medication Container Assemblies

Referring now to FIGS. 7A and 7B, which are simplified illustrations of a schematic view and a perspective view of a medication container assembly, according to some embodiments of the invention.

According to some embodiments, the medication container assemblies coupled to the medication panel are identical. In some embodiments, the medication container assemblies coupled to the panel vary in size. In some embodiments, the medication container assemblies coupled to the medication panel vary in shape. According to some embodiments, the medication container assemblies accommodate different types/forms of medication. In some embodiments, the size and the shape of the medication container assemblies are in according to the medication type/form.

According to some embodiments, medication container assembly 702 includes a canister 704 and a medication collection chamber 706 formed within canister 704 and configured to accommodate medication to be picked by a gripping assembly.

According to some embodiments, medication is stored in a medication cartridge 708, prior to providing medication in container assembly 702. In some embodiments, transferring medication stored in cartridge 708 to container assembly 702 (e.g. in direction M1) is by attaching cartridge 708 to canister 704. In some embodiments, a collection chamber 706 is formed within canister 704 to collect medication M from cartridge 708. In some embodiments, medication M drop from cartridge 708 into collection chamber 706 after the attachment of cartridge 708 to canister 704. In some embodiments, container assembly 702 does not include cartridge, and medication M is supplied to collection chamber 706 by a port at canister 704.

According to some embodiments, medication container assembly 702 has a detachable probe 710 coupled to canister 704 for picking medication dosage M from collection chamber 706. In some embodiments, extracting medication dosage is by grabbing dispensing probe 710 out of medication container 702 by a gripping assembly (such as 106).

In some embodiments, probe 710 has a tip 712 at its distal end. In some embodiments, tip 712 is configured to be disposed within collection chamber 706, so that probe 710 can access medication disposed with chamber 706. According to some embodiments, picking medication dosage by tip 712 from collection chamber 706 is by applying suction through tip 712. In some embodiments, suction is applied by the gripping assembly, and probe 710 is at least partially hollow to transfer suction to tip 712. According to some embodiments, releasing the medication dosage picked by probe 710 is by terminating the suction.

In some embodiments, probe 710 is configured to pick medication by a grasping element (e.g. a grasping claw). In some embodiments, the grasping element coupled at tip 712. In some embodiments, grasping by probe 710 is without applying suction via probe 710.

Increasing the availability of medication dosage in proximity to the probe 710 can increasing the predictability of the percentage of medication extracted out of collection chamber 706 of container assembly 702. According to some embodiments, collecting medication dosage in proximity to the probe 710 can be by sliding medication within container 702 using gravity (e.g. in direction M2).

According to some embodiments, as shown for example in FIG. 7B, collection chamber 706 has one or more slanted medication guiding surfaces 726. In some embodiments, at least one guiding surface 726-1 is slanted towards tip 712 of probe 710 to direct medication dosage within the container assembly 702 towards tip 712. In some embodiments, guiding surface 726-1 is divided into two or more surfaces 726-2 and 726-3, which direct medication toward the center of guiding surface 726-1.

According to some embodiments, described elsewhere herein (for example as shown FIGS. 3D and 5), the collection chamber is coupled in a slanted orientation to the medication panel for guiding the medication dosage by gravity towards the tip of the probe. In some embodiments, collection chamber has one or more guiding surface shaped and oriented for guiding medication dosage by gravity when the medication assembly is coupled to the medications panel.

According to some embodiments, guiding medication dosage towards tip 712 of probe 710 is by apply positive or negative pressure differential within container 702. In some embodiment, a negative pressure is by suction.

According to some embodiments, viewing the content of chamber 706 while container assembly 702 is at the panel 700 is beneficial for an operator. According to some embodiments, at least one wall of chamber 706 is transparent to allowing viewing of medication collected within chamber 706. In some embodiments, the transparent wall is the wall facing a side of panel 700, which is visible by an operator. A potential advantage is viewing by the operator the content of the container while the container is at the panel.

According to some embodiments, probe 710 is detachably connected to canister 704 by a probe connector 728. In some embodiments, picking probe 710 out of container 702 is by gripping probe connector 728 by the gripping assembly. In some embodiments, the distal end 730 of probe 710 is connected to probe connector 728. In some embodiments, a suction is applied by the gripping assembly through distal end 730 of probe 710 for picking medication dosage within collector chamber 706.

According to some embodiments, container assembly 702 includes a medication collection dam 732 for controlling the amount of medication accumulated in proximity to tip 712.

According to some embodiments, container assembly 702 is made of anti-static material. In some embodiments, canister 704 is made of anti-static material.

According to some embodiments, container assemblies, such as 702 have one or more indication/alert circuits (e.g. 736 in FIG. 7B) to identify/report operational parameters. According to some embodiments, indication provided by containers assemblies 702 is visual. In some embodiments, a visual indication is provided with light. In some embodiments, a visual indication is by led disposed on or within the container assembly. In some embodiments, transferring light to indicator 736 is by using a light pipe. In some embodiments, indications provides by indicator 736 are in two or more colors. In some embodiments, alerts include soundwaves. In some embodiments, alerts include vibrations. In some embodiments, the panel (as any one of the panels disclosed elsewhere herein) include one or more indicators.

In some embodiments, the dispensing system include a monitor having one or more alerting devices.

In some embodiments, the medication container assembly has one or more chips or RFID tags 738. In some embodiments, RFID/chips 738 store/transmit operational parameters of the medication container assembly.

Some examples of indications related to container assemblies are: cartridge connection state, medications in container, probe attachment state, indications to guide steps in preparation of medication container assembly, etc.

According to some embodiments, one or more of the medication container assemblies comprise electrical/electromagnetic circuit to transmit operational parameters of the medication container assemblies, such as: a need to replace container, an error related to container, an empty container, low medication content than a predefined value, and normal operation.

Example Embodiments of Rotating Gripping Assembly

Figure 8A:
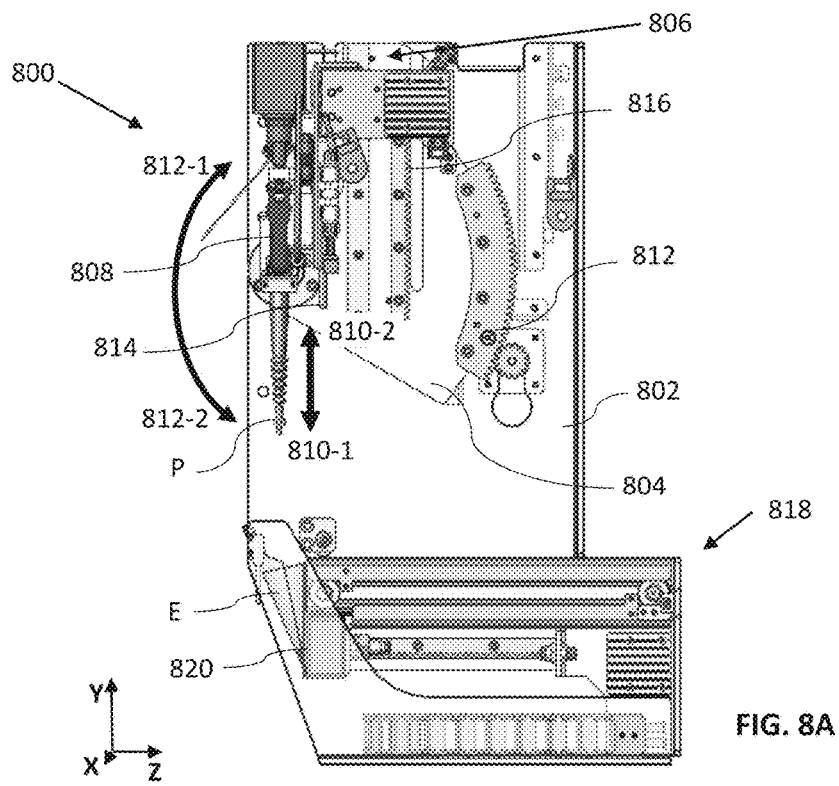
FIGS. 8A-8C are simplified illustrations of a side view of a gripping assembly, according to some embodiments of the invention.
Figure 8B:
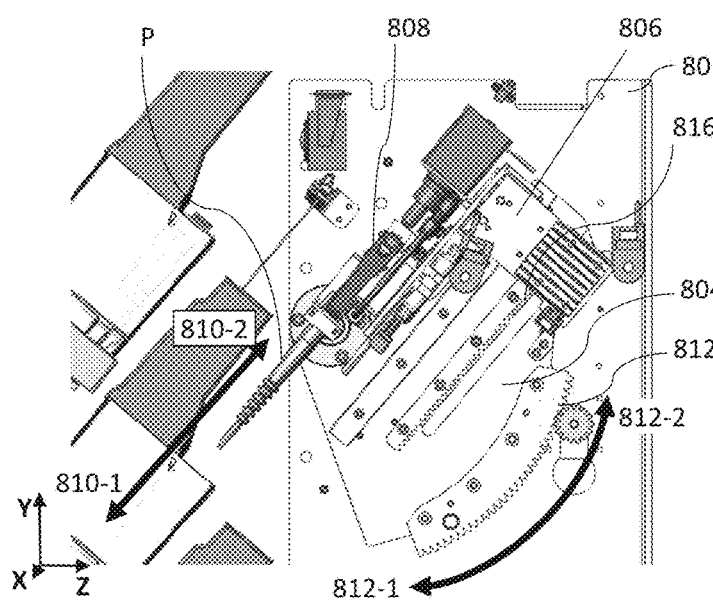
Figure 8C:
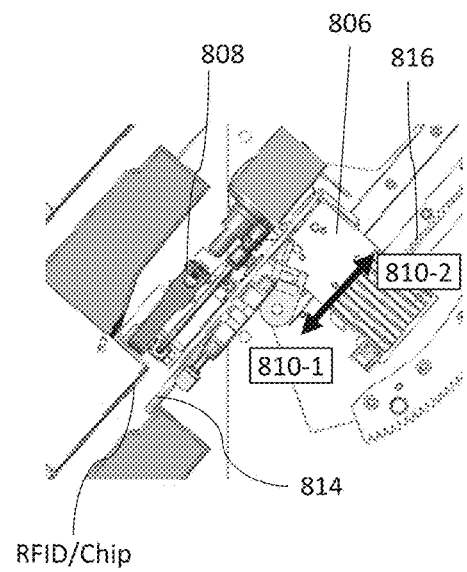

Referring now to FIGS. 8A-8C, which are simplified illustrations of a side view of a gripping assembly, according to some embodiments of the invention.

As shown in FIGS. 8A and 8B, gripping assembly 800 includes a housing 802. In some embodiments, gripping assembly 800 has a movable platform 804, rotatably coupled to housing 802.

According to some embodiments, gripping assembly 800 includes a gripper platform 804, and a gripper 808 coupled to platform 804. In some embodiments, gripper 808 is configured for picking a probe P coupled to a medication container assembly.

As shown in FIGS. 8A to 8C, in some embodiments, gripper 808 is linearly moveable in respect to housing 802 in a proximal direction 810-1 and a distal direction 810-2. In some embodiments, one or more gripper actuators actuate gripper 808 to grab probe P from a medication container assembly by approximating gripper 808 to the probe P in a proximal direction 810-1, and grabbing probe P away of the container assembly by a distal linear motion in direction 810-2. In some embodiments, returning of probe P to the medication container assembly is by actuating gripper 808 by gripper in a proximal linear motion towards of the medication container assembly in direction 810-1. In some embodiments, moving gripper 808 in proximal direction 810-1 and distal direction 810-2 is without moving housing 802 in respect to the medication panel (such one of the panels described elsewhere herein). In some embodiments, proximal direction 810-1 and distal direction 810-2 are vertical in direction Y.

According to some embodiments, rotating gripper 808 in respect to the medication panel is performed without rotating housing 802. In some embodiments, rotating gripper 808 in respect to the medication panel is without moving gripping assembly 800 in respect to the medication panel. In some embodiments, for example as shown in FIGS. 8A and 8B, gripping assembly 800 includes one or more gear mechanisms 812, interconnecting platform 804 and housing 802. In some embodiments, rotating of gripper 808 is by rotating gripper platform 804. In some embodiments, gripping assembly 800 includes one or more gear mechanisms 812, confirmed to rotate gripper 808 in directions 812-1 and 812-2 (shown in FIGS. 8A and 8B). In some embodiments, rotational directions 812-1 and 812-2 are about axis X which is perpendicular to axes Y and Z.

According to some embodiments, gripping assembly 800 is configured to update information encoded in the medication container assembly. As shown in FIGS. 8A and 8C, gripping assembly 800 includes a RFID/tag reader and/or encoder 814, coupled to gripper 808. In some embodiments, gripper 808 is configured to actuate reader/encoder 814 in a proximal direction 810-1 and a distal 810-2 direction, to enable approximating and detracting to/from an RFID tag/Chip coupled to a medication container assembly. In some embodiments, reader/encoder 814 is movable in respect to housing 802.

In some embodiments, for example as in FIGS. 8A to 8C, reader/encoder 814 is configured to move together with gripper 808, for example, for approximating RFID tag/Chip of container, while picking probe P by gripper 808. In some alternative embodiments, reader/encoder 814 is configured to move independently of gripper 808.

In some embodiments, gripping assembly 800 includes one or more linear gear mechanisms 816, interconnecting gear module 808 and housing 802. In some embodiments, moving of gear module 808 by gear 816, moves gripper 808 in directions 810-1 (shown in FIG. 8C) and 810-2 (shown in FIGS. 8A and 8B). In some embodiments, linear gear mechanism 816 interconnects gear module 808 and gripper platform 804. In some embodiments, connecting gear 816 to gripper platform 804, enables actuating of gripper 808 and/or reader 814 in both linear and rotation motion in respect to housing 802.

According to some embodiments, gripping assembly 800 includes envelope carrier 818 for coupling one or more medication envelopes E to gripping assembly 800. In some embodiments, for example as shown in FIG. 8A, envelope carrier 818 is coupled to housing 802, below gripper 808. According to some embodiments, envelope carrier 818 includes envelope mount 820, which is configured to hold one or more envelopes E when dispensing medication dosage into envelope E. As shown in FIG. 8A, envelope mount 820, is holding envelope E vertically under gripper 808. In some embodiments, when a probe P is used to hold a medication dosage, envelope mount 820, is holding envelope E vertically below the tip of probe P, such that a medication disposed at the tip of probe P is dispensed by dropping the medication from the probe P into the open envelope.

In some embodiment, holding envelope E by carrier 818 is by suction power applied to a surface of the envelope by mount 820. In some embodiments, provide suction to envelope carrier 818 is by a suction system is connected gripping assembly 800.

General

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As used herein with reference to quantity or value, the term "about" means "within ±5% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority documents of this application are hereby incorporated herein by reference in their entirety. In addition, any priority document(s) of this application is/are hereby incorporated herein by reference in its/their entirety.

What is claimed is:

1. A medication dispensing system, comprising:
one or more medication panels, each having a plurality of docking ports located at a vertical displacement one from another;
a plurality of medication container assemblies for storing medication, coupled to said plurality of docking ports;
one or more actuators;
a gripping assembly, movable vertically by said one or more actuators to a proximate one or more of said medication container assemblies for picking a medication dosage out of said one or more of said medication container assemblies; and
a receptacle carrier, comprising a receptacle mount for holding one or more medication receptacles configured to receive said medication dosage;
wherein said one or more medication panels comprise one or more port surfaces; and said plurality of docking ports are coupled to said port surfaces, and protrude in a general docking port direction, which is transverse to said one or more port surfaces in an acute angle.

2. A medication dispensing system according to claim 1, said receptacle carrier is coupled to said gripping assembly for holding one or more medication receptacles to have an overlap between a projection of a medication container assembly on a vertical plane, with a projection of said receptacle on a vertical plane, after said picking of said mediation dosage out of said medication container assembly.

3. A medication dispensing system according to claim 1, wherein said receptacle carrier is coupled to said gripping assembly for holding one or more medication receptacles below said medication dosage.

4. A medication dispensing system according to claim 1, wherein said plurality of medication container assemblies extend along a general container direction, which is transverse to a vertical plane in an acute angle.

5. A medication dispensing system according to claim 1, wherein:
said plurality of docking ports comprise a docking surface, which is transverse to a vertical plane in an acute angle.

6. A medication dispensing system according to claim 1, wherein said one or more medication panels are slanted in respect to a vertical plane.

7. A medication dispensing system according to claim 1, wherein said medication container assemblies are stationary in respect to said one or more medication panels, when coupled to said plurality of docking ports.

8. A medication dispensing system according to claim 1, wherein said receptacle carrier is movable vertically by said one or more actuator to approximate one or more of said medication container assemblies.

9. A medication dispensing system according to claim 1, wherein said medication container assemblies comprise:
a canister, comprising:
a mounting rim, shaped and sized to couple the medication container assembly to one of said docking ports;
a medication collection chamber, having a guiding surface defining a portion of a bottom portion of said chamber;
a cartridge for storing medication, coupled to said canister and having a medication release port;
a gripping port to insert a probe for extracting said medication dosage; and
wherein the guiding surface is sloped from a point located underneath the medication release port to a point located underneath the gripping port.

10. A medication dispensing system according to claim 1, wherein said gripping assembly comprises:
a gripper platform; and
a gripper, movably coupled to said gripper platform, to move said gripper in respect to said one or more medication container assemblies.

11. A medication dispensing system according to claim 1, wherein one or more of the medication container assemblies is accessible by an operator while the gripping assembly is in motion.

12. A medication dispensing system according to claim 1, wherein one or more of the medication container assemblies comprise electrical/electromagnetic circuit to transmit operational parameters of the medication container assemblies.

13. A medication dispensing system according to claim 1, wherein vertically adjacent medication container assemblies have an overlap between a projection of a medication container assembly on a vertical plane, with a projection of another vertically adjacent medication container assembly on a vertical plane.

14. A medication dispensing system according to claim 13, wherein said overlap is greater than 10% of a projection of one or more of said vertically adjacent medication container assemblies on said vertical plane.

15. A method for dispensing medication dosage, by a system having medication container assemblies for storing medication, the method comprises:
identifying a medication container assembly storing a selected medication, said medication container assembly is positioned in a vertical displacement to one or more medication container assemblies;
approximating a gripping assembly to said medication container assembly by moving said gripping assembly vertically towards said medication container assembly;
manipulating said gripping assembly to extract medication dosage out of said medication container assembly; and
dispensing dosage into one or more medication receptacles;
wherein said manipulating comprises:
rotating at least a portion of said gripping assembly to be angular to a vertical plane;
picking said medication dosage by a probe inserted within said medication container assembly;
detaching said probe outside said medication container assembly; and
positioning said dosage above an opening in said medication receptacle.

16. A method for dispensing medication dosage according to claim 15, wherein said approximating includes manipulating one or more medication receptacles together with said gripping assembly.

17. A method for dispensing medication dosage according to claim 15, comprising manipulating a medication receptacle carrier to position said medication receptacle under said gripping assembly.

18. A method for dispensing medication dosage according to claim 15, wherein the time between said identifying and said dispensing is less than 1 sec.

19. A method for dispensing medication dosage according to claim 15, comprising:
moving said receptacle vertically to approximate said gripping assembly.

20. A method for dispensing medication dosage according to claim 15, comprising:
moving said receptacle vertically to approximate said medication container assembly.

21. A method for dispensing medication dosage according to claim 20, wherein said moving is prior to said dispensing.

22. A method for dispensing medication dosage according to claim 20, wherein said moving is prior to said manipulating.

23. A medication dispensing system, comprising:
one or more medication panels, each having a plurality of docking ports located at a vertical displacement one from another;
a plurality of medication container assemblies for storing medication, coupled to said plurality of docking ports;
one or more actuators;
a gripping assembly, movable vertically by said one or more actuators to a proximate one or more of said medication container assemblies for picking a medication dosage out of said one or more of said medication container assemblies; and
a receptacle carrier, comprising a receptacle mount for holding one or more medication receptacles configured to receive said medication dosage;
wherein said medication container assemblies comprise:
a canister, comprising:
a mounting rim, shaped and sized to couple the medication container assembly to one of said docking ports;
a medication collection chamber, having a guiding surface defining a portion of a bottom portion of said chamber;
a cartridge for storing medication, coupled to said canister and having a medication release port;
a gripping port to insert a probe for extracting said medication dosage; and
wherein the guiding surface is sloped from a point located underneath the medication release port to a point located underneath the gripping port.

24. A medication dispensing system according to claim 23, wherein said plurality of medication container assemblies extend along a general container direction, which is transverse to a vertical plane in an acute angle.

25. A medication dispensing system according to claim 23, wherein:
said one or more medication panels comprise one or more port surfaces; and
said plurality of docking ports are coupled to said port surfaces, and protrude in a general docking port direction, which is transverse to said one or more port surfaces in an acute angle.

26. A medication dispensing system according to claim 23, wherein:
said plurality of docking ports comprise a docking surface, which is transverse to a vertical plane in an acute angle.

27. A medication dispensing system according to claim 23, wherein said receptacle carrier is movable vertically by said one or more actuator to approximate one or more of said medication container assemblies.

28. A medication dispensing system according to claim 23, wherein one or more of the medication container assemblies is accessible by an operator while the gripping assembly is in motion.

29. A medication dispensing system according to claim 23, wherein one or more of the medication container assemblies comprise electrical/electromagnetic circuit to transmit operational parameters of the medication container assemblies.

30. A medication dispensing system according to claim 23, said receptacle carrier is coupled to said gripping assembly for holding one or more medication receptacles to have an overlap between a projection of a medication container assembly on a vertical plane, with a projection of said receptacle on a vertical plane, after said picking of said mediation dosage out of said medication container assembly.

* * * * *